United States Patent
Onishi et al.

(10) Patent No.: US 9,867,593 B2
(45) Date of Patent: *Jan. 16, 2018

(54) PROCESSING DEVICE, ULTRASONIC DEVICE, ULTRASONIC PROBE, AND ULTRASONIC DIAGNOSTIC DEVICE

(71) Applicant: SEIKO EPSON CORPORATION, Tokyo (JP)

(72) Inventors: Yasunori Onishi, Nagano (JP); Jiro Tsuruno, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/366,135

(22) Filed: Dec. 1, 2016

(65) Prior Publication Data

US 2017/0079618 A1    Mar. 23, 2017

Related U.S. Application Data

(63) Continuation of application No. 13/903,518, filed on May 28, 2013, now Pat. No. 9,554,773.

(30) Foreign Application Priority Data

May 29, 2012    (JP) ................................ 2012-121889

(51) Int. Cl.
*A61B 8/00* (2006.01)
*G01S 7/52* (2006.01)
(Continued)

(52) U.S. Cl.
CPC .......... *A61B 8/4444* (2013.01); *A61B 8/4405* (2013.01); *A61B 8/4411* (2013.01);
(Continued)

(58) Field of Classification Search
CPC ....... A61B 8/444; A61B 8/461; A61B 8/4494; A61B 8/4477; A61B 8/4483; A61B 8/4405
See application file for complete search history.

(56) References Cited

U.S. PATENT DOCUMENTS 5,307,816 A     5/1994  Hashimoto et al.
2006/0293595 A1  12/2006  Clark et al.
(Continued)

FOREIGN PATENT DOCUMENTS

EP    1629778 A1    3/2006
JP    05-220152 A   8/1993
(Continued)

*Primary Examiner* — Joseph M Santos Rodriguez
(74) *Attorney, Agent, or Firm* — Global IP Counselors, LLP

(57) ABSTRACT

An ultrasonic device includes a substrate, first ultrasonic elements having a resonance characteristic of a first frequency, and second ultrasonic elements having a resonance characteristic of a second frequency lower than the first frequency. The first ultrasonic elements are arranged along a first direction to make a first to an n-th high-frequency ultrasonic element lines. The second ultrasonic elements are arranged along the first direction to make a first to an n-th low-frequency ultrasonic element lines. The first to the n-th high-frequency ultrasonic element lines and the first to the n-th low-frequency ultrasonic element lines are arranged along a second direction. The first and second ultrasonic elements have an opening, a vibrating membrane, and a piezo element part. A length in the second direction of the opening of the first ultrasonic element is shorter than a length in the second direction of the opening of the second ultrasonic element.

6 Claims, 13 Drawing Sheets

(51) Int. Cl.
    *G01S 15/89*      (2006.01)
    *B06B 1/02*       (2006.01)
    *B06B 1/06*       (2006.01)

(52) U.S. Cl.
    CPC .......... *A61B 8/4427* (2013.01); *A61B 8/4477* (2013.01); *A61B 8/4483* (2013.01); *A61B 8/4494* (2013.01); *A61B 8/461* (2013.01); *A61B 8/54* (2013.01); *B06B 1/0269* (2013.01); *B06B 1/0622* (2013.01); *G01S 7/5202* (2013.01); *G01S 7/52046* (2013.01); *G01S 15/895* (2013.01); *G01S 15/8925* (2013.01); *G01S 7/5205* (2013.01)

(56)　　　　　　References Cited

U.S. PATENT DOCUMENTS

| | | |
|---|---|---|
| 2011/0263982 A1 | 10/2011 | Kano |
| 2011/0319766 A1 | 12/2011 | Tsuruno |
| 2014/0276080 A1 | 9/2014 | Kano |

FOREIGN PATENT DOCUMENTS

| | | |
|---|---|---|
| JP | 2000-152930 A | 6/2000 |
| JP | 2003-169800 A | 6/2003 |
| JP | 2003-339700 A | 12/2003 |
| JP | 2006-061252 A | 3/2006 |
| JP | 2007-503243 A | 2/2007 |
| JP | 2007-232638 A | 9/2007 |
| JP | 2008-043529 A | 2/2008 |
| JP | 2011-234073 A | 11/2011 |
| JP | 2012-005690 A | 1/2012 |

PROCESSING DEVICE, ULTRASONIC DEVICE, ULTRASONIC PROBE, AND ULTRASONIC DIAGNOSTIC DEVICE

CROSS-REFERENCE TO RELATED APPLICATIONS

This application is a divisional application of U.S. patent application Ser. No. 13/903,518 filed on May 28, 2013, which claims priority to Japanese Patent Application No. 2012-121889 filed on May 29, 2012. The entire disclosures of U.S. patent application Ser. No. 13/903,518 and Japanese Patent Application No. 2012-121889 are hereby incorporated herein by reference.

BACKGROUND

Technical Field

The present invention relates to an ultrasonic device, an ultrasonic probe, and an ultrasonic diagnostic device.

Related Art

As devices that irradiate an ultrasonic wave toward an object and receive a reflected wave from interfaces having different acoustic impedance in an internal object, for example, ultrasonic diagnostic apparatuses for inspecting the inside of the human body are well known. As ultrasonic devices (ultrasonic probes) used for ultrasonic diagnostic devices, for example, Patent Document 1 discloses a matrix array pattern arrangement of piezo elements and a method for outputting an ultrasonic wave.

Japanese Laid-open Patent Publication No. 2006-61252 (Patent Document 1) is an example of the related art.

SUMMARY

Problems to be Solved by the Invention

However, in this method, a driving signal cannot be changed in response to a distance between an ultrasonic probe and an object so that the reduction of the resolution occurs depending on a distance to an object. Therefore, a plurality of ultrasonic probes is used properly in response to a distance to an object. According to some aspects of the invention, an ultrasonic device, an ultrasonic probe, an ultrasonic diagnostic device, and the like that can drive a signal in response to a distance to an object can be provided.

Means Used to Solve the Above-Mentioned Problems

According to one aspect of the invention, an ultrasonic device includes a substrate, a plurality of first ultrasonic elements having a resonance characteristic of a first frequency disposed on the substrate, and a plurality of second ultrasonic elements having a resonance characteristic of a second frequency, which is lower than the first frequency, disposed on the substrate. The plurality of first ultrasonic elements are arranged along a first direction to make a first high-frequency ultrasonic element line to an n-th high-frequency ultrasonic element line (n is an integer of more than 2). The plurality of second ultrasonic elements are arranged along the first direction to make a first low-frequency ultrasonic element line to an n-th low-frequency ultrasonic element line. The first high-frequency ultrasonic element line to the n-th high-frequency ultrasonic element line are arranged along a second direction which intersects with the first direction. The first low-frequency ultrasonic element line to the n-th low-frequency ultrasonic element line are arranged along the second direction. Each of the first ultrasonic elements and each of the second ultrasonic elements have an opening provided in the substrate, a vibrating membrane that covers the opening, and a piezo element part provided on the vibrating membrane. A length in the second direction of the opening of each of the first ultrasonic elements is shorter than a length in the second direction of the opening of each of the second ultrasonic elements.

BRIEF DESCRIPTION OF THE DRAWINGS

Referring now to the attached drawings which form a part of this original disclosure.

DETAILED DESCRIPTION OF EXEMPLARY EMBODIMENTS

Hereinafter, the preferred embodiments of the invention will be explained in detail. By the way, the embodiments explained below shall not be construed as unreasonably limiting the subject matter of the invention described in the claims, and all the elements explained in the embodiments are not necessarily essential to the solving means of the invention.

1. Ultrasonic Element

Figure 1A:
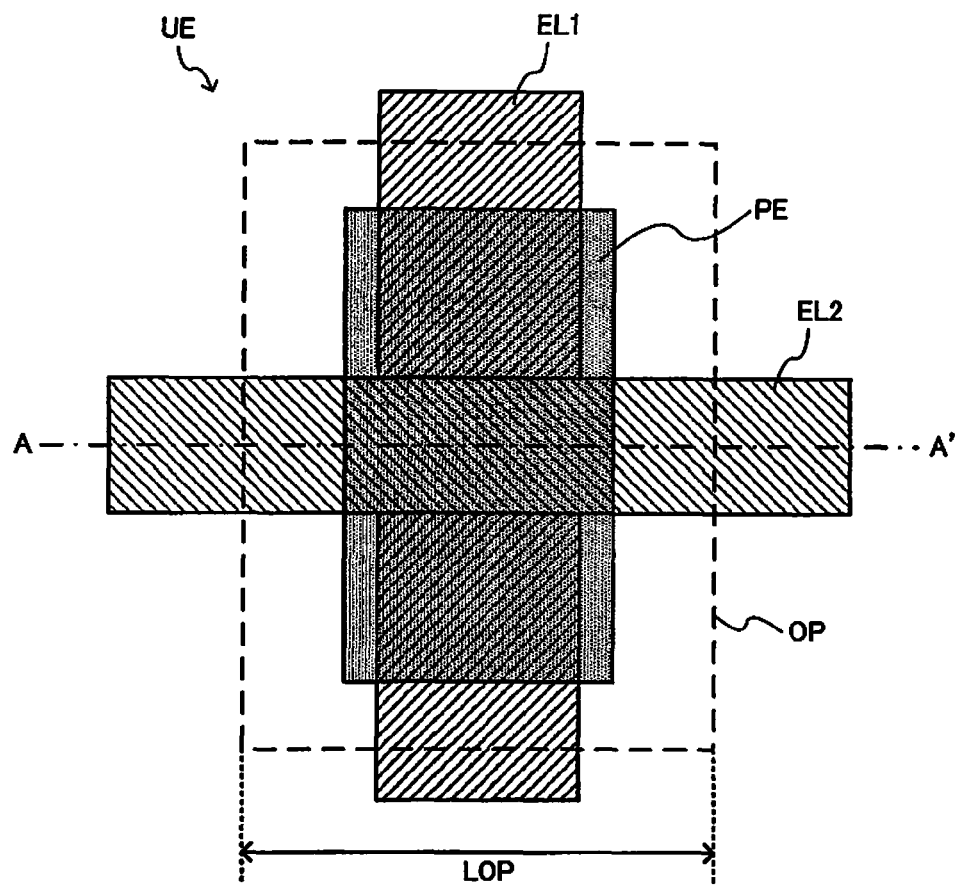
FIG. 1A and FIG. 1B show basic configuration examples of ultrasonic elements.
Figure 1B:
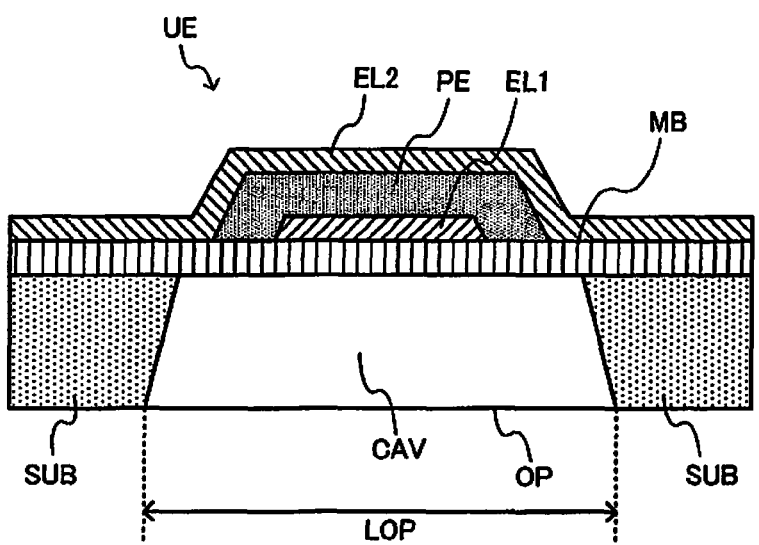

FIG. 1A and FIG. 1B show a basic configuration example of an ultrasonic element UE including an ultrasonic device of the present embodiment. The ultrasonic element UE of the present embodiment has a vibrating membrane (membrane, supporting member) MB, and a piezo element part. The piezo element part has a lower electrode (first electrode layer) EL1, a piezoelectric body film (piezoelectric body layer) PE, and an upper electrode (second electrode layer) EL2. By the way, the ultrasonic element UE of the present embodiment is not limited to the configuration of FIG. 1 so that various modifications omitting a part of the configuration elements, replacing to other configuration elements, adding other configuration elements, and the like can be possible.

FIG. 1A is a plan view of the ultrasonic element UE formed on a substrate (silicon substrate) SUB. The plan view is a view from a direction perpendicular to the substrate in the element forming surface side. FIG. 1B is a cross-section view showing a cross-section along A-A' of FIG. 1A.

The first electrode layer EL1 is formed on an upper layer of the vibrating membrane MB by, for example, a metal thin film. This first electrode layer EL1 extends to outside of the element forming area as shown in FIG. 1A and it can be a wire connecting to an adjacent ultrasonic element UE.

The piezoelectric body film PE is formed by for example, a PZT (zirconate titanate) thin film, and it is provided to cover at least a part of the first electrode element EL1. By the way, the material of the piezoelectric body film PE is not limited to PZT, and for example, lead titanate ($PbTiO_3$), lead zirconate ($PbZrO_3$), lead titanate lantern ($(Pb, La) TiO_3$), and the like can be used.

The second electrode layer EL2 is formed by for example, a metal thin film, and it is provided to cover at least a part of the piezoelectric body film PE. The second electrode layer EL2 extends to outside of the element forming area as shown in FIG. 1A, and it can be a wire connecting to an adjacent ultrasonic element UE.

The vibrating membrane (membrane) MB configured by, for example, two layers of $SiO_2$ thin film and $ZrO_2$ thin film is provided to cover an opening OP. The vibrating membrane MB supports the piezoelectric body film PE and the first and second electrode layers EL1, EL2, and also, it vibrates in accordance with expansion and contraction of the piezoelectric body film PE so that it can generate ultrasonic wave.

A cavity area CAV is formed by etching such as the reactive ion etching (RIE), or the like from the back surface (surface on which the element is not formed) side of the silicon substrate SUB. An ultrasonic wave is outputted from the opening OP of the cavity area CAV.

The lower electrode of the ultrasonic element UE is formed by the first electrode layer EL1, and the upper electrode is formed by the second electrode layer EL2. Concretely, a part of the first electrode layer EL1 covered by the piezoelectric body film PE forms the lower electrode, and a part of the second electrode layer EL2 covered by the piezoelectric body film PE forms the upper electrode. That is, the piezoelectric body film PE is provided between the lower electrode and the upper electrode.

The voltage is impressed between the lower electrode and the upper electrode, that is, between the first electrode layer EL1 and the second electrode layer EL2 so that the piezoelectric film PE expands and contracts in-plane direction. One surface of the piezoelectric body film PE connects to the vibrating membrane MB through the first electrode layer EL1. The second electrode layer EL2 is formed on the other surface of the piezoelectric body film PE, but another layer is not formed on the second electrode layer EL2. Because of this, the vibrating membrane MB side of the piezoelectric film PE is difficult to perform expansion and contraction, and the second electrode layer EL2 side of the piezoelectric film PE becomes easy to perform expansion and contraction. Accordingly, when the voltage is impressed to the piezoelectric body film PE, the deflection occurs as convex on the cavity area CAV side so that the vibrating membrane MB deflects. The vibrating membrane MB vibrates in a film thickness direction by impressing AC voltage to the piezoelectric body film PE so that the ultrasonic wave is outputted from the opening OP by the vibration of the vibrating membrane MB. The voltage impressing to the piezoelectric body film PE is, for example, 10 to 30V, and the frequency is, for example, 1 to 10 MHz.

The ultrasonic element UE has a resonance characteristic determined by the length LOP of the short side of the opening OP. As the length of the short side of the opening is longer, the frequency of resonance becomes lower, and as the length of the short side of the opening is shorter, the frequency of resonance becomes higher. The length LOP of the short side of the opening OP providing an ultrasonic element UE that has a resonance characteristic of the first frequency is shorter than the length LOP of the short side of the opening OP providing an ultrasonic element UE that has a resonance characteristic of the second frequency which is lower than the first frequency.

The phrase "the ultrasonic element UE has a resonance characteristic of the first frequency" means that the ultrasonic wave outputted from the ultrasonic element UE has a peak in the first frequency.

As described later, in the ultrasonic device 100 of the present embodiment, by providing two types of ultrasonic elements having different length LOP of the short side of the opening OP, an ultrasonic element having high resonance frequency and an ultrasonic element having low resonance frequency can be mixedly arranged on one substrate.

Figure 2A:
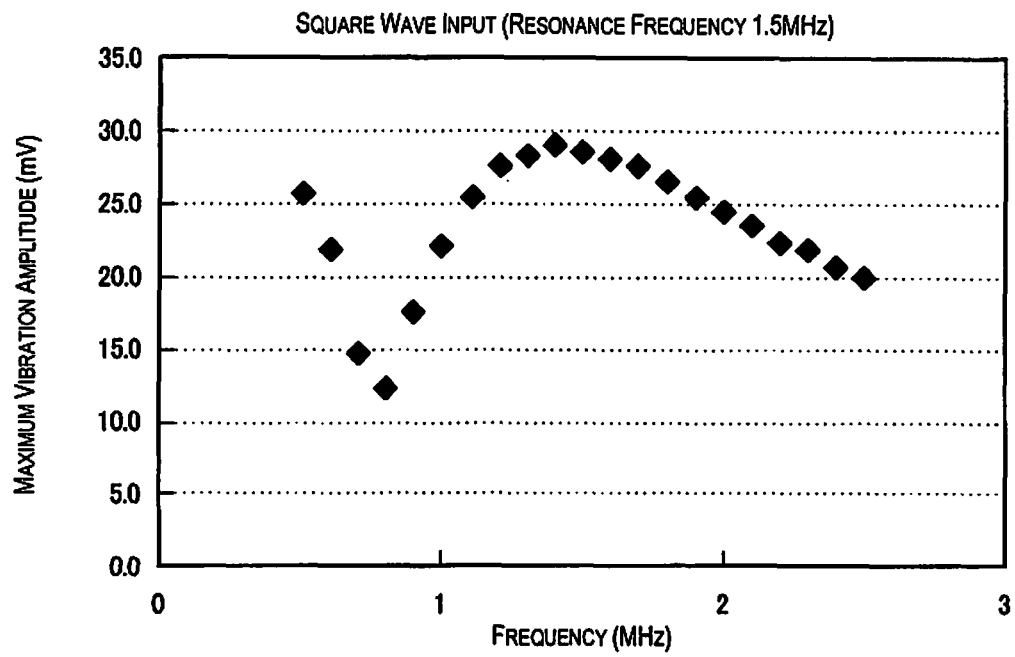
FIG. 2A and FIG. 2B show a maximum amplitude of ultrasonic waves outputted in a case that a square wave and a sine wave are inputted to an ultrasonic element of resonance frequency 1.5 MHz.
Figure 2B:
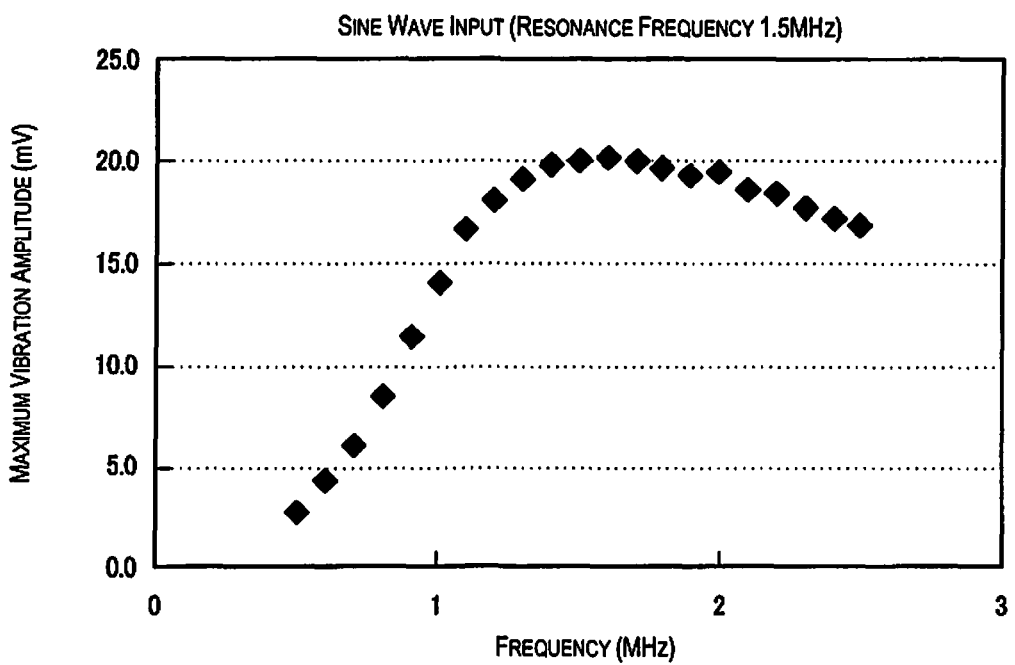

As a signal (driving signal) that is impressed to the piezoelectric body film PE of the ultrasonic element UE, for example, a square wave, a sine wave, or the like can be used. FIG. 2A and FIG. 2B show a maximum amplitude of ultrasonic waves outputted in a case that a square wave and a sine wave are inputted to an ultrasonic element of resonance frequency 1.5 MHz. The horizontal axis is the frequency of the inputted square wave or the inputted sine wave.

As shown in FIG. 2A, in a case of the square wave input, the maximum amplitude becomes a peak at resonance frequency 1.5 MHz and its vicinity. In addition, the maximum amplitude becomes larger at the lower frequency region (lower than 1.8 MHz). On the other hand, as shown in FIG. 2B, in a case of the sine wave input, the maximum amplitude becomes a peak at resonance frequency 1.5 MHz and its vicinity and the maximum amplitude is reduced at the lower frequency region. Also, when the maximum amplitudes at the vicinity of resonance frequency 1.5 MHz are compared, the case that the square wave is inputted is larger than the case that the sine wave is inputted.

Figure 3A:
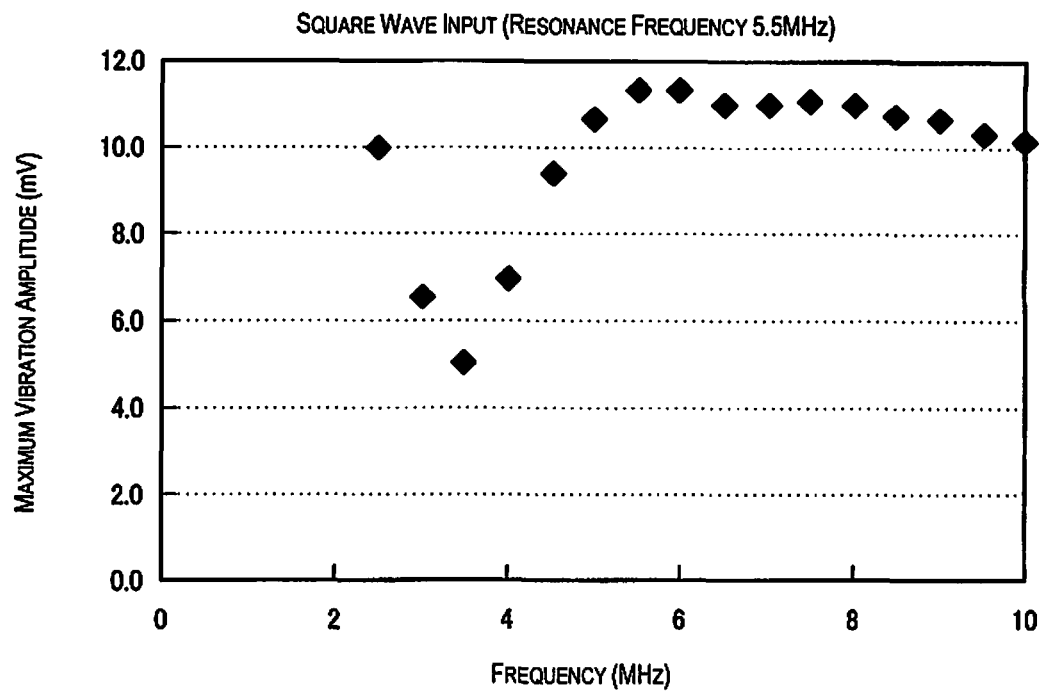
FIG. 3A and FIG. 3B show a maximum amplitude of ultrasonic waves outputted in a case that a square wave and a sine wave are inputted to an ultrasonic element of resonance frequency 5.5 MHz.
Figure 3B:
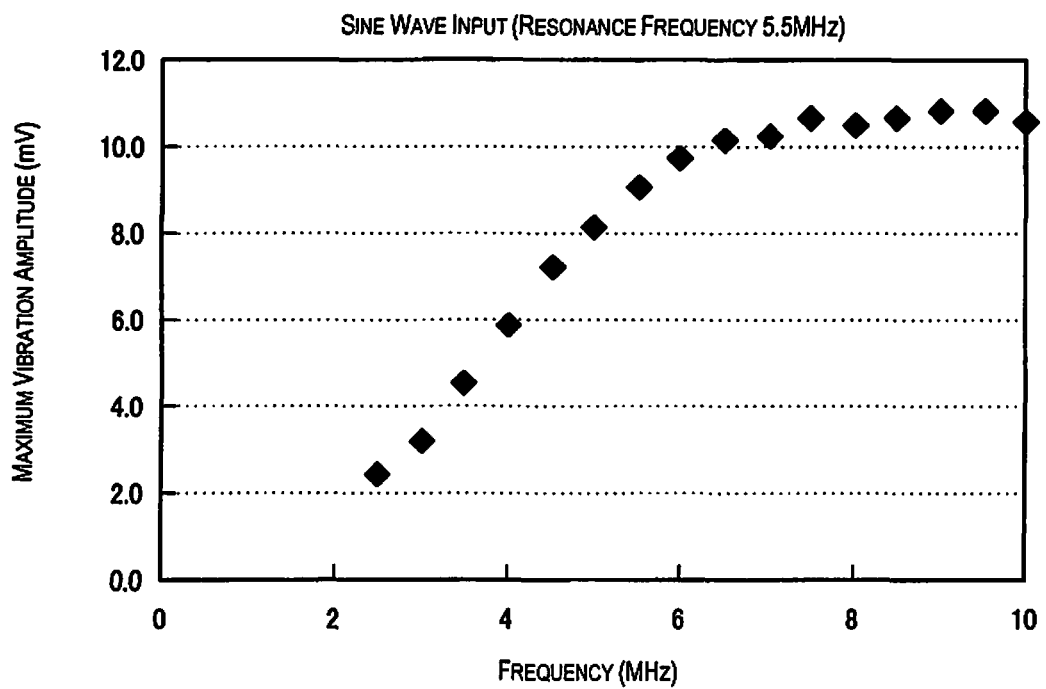

FIG. 3A and FIG. 3B show a maximum amplitude of ultrasonic waves outputted in a case that a square wave and a sine wave are inputted to an ultrasonic element of resonance frequency 5.5 MHz. As shown in FIG. 3A, in a case of the square wave input, the maximum amplitude becomes a peak at resonance frequency 5.5 MHz and its vicinity. In addition, the maximum amplitude becomes larger at the lower frequency region (lower than 2.6 MHz). On the other hand, as shown in FIG. 3B, in a case of the sine wave input, the maximum amplitude becomes high at resonance frequency 5.5 MHz and its vicinity and the maximum amplitude is reduced at the lower frequency region. Also, when the maximum amplitudes at the vicinity of resonance frequency 5.5 MHz are compared, there are no significant differences between the case that the square wave is inputted and the case that the sine wave is inputted.

In this manner, in a case that the ultrasonic element of lower resonance frequency (e.g., 1.5 MHz) is driven, it is better to input the square wave so that a high ultrasonic intensity can be obtained. In a case that a distance between the ultrasonic element and an object is far, the high ultrasonic intensity is required to obtain the desired resolution because the intensity is attenuated when an ultrasonic wave outputted from the ultrasonic element reaches to the object and the reflected wave is returned to the ultrasonic element. Also, the ultrasonic wave of the lower frequency is smaller attenuation than the ultrasonic wave of the higher frequency in a medium. From the above description, in a case that the distance between the ultrasonic element and the object is far, to obtain the desired resolution, it has an advantage that the ultrasonic element that the resonance frequency is low is driven by the square wave.

Figure 4A:
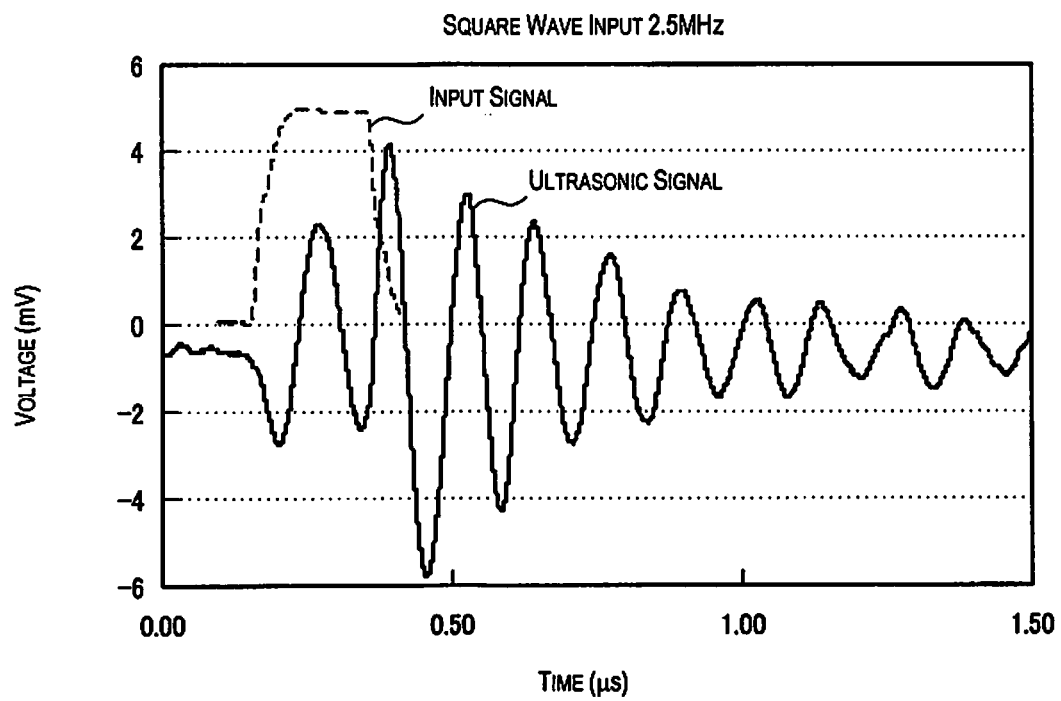
FIG. 4A and FIG. 4B show an ultrasonic signal waveform in a case that a square wave of frequencies 2.5 MHz and 5.5 MHz is inputted to an ultrasonic element of resonance frequency 5.5 MHz.
Figure 4B:
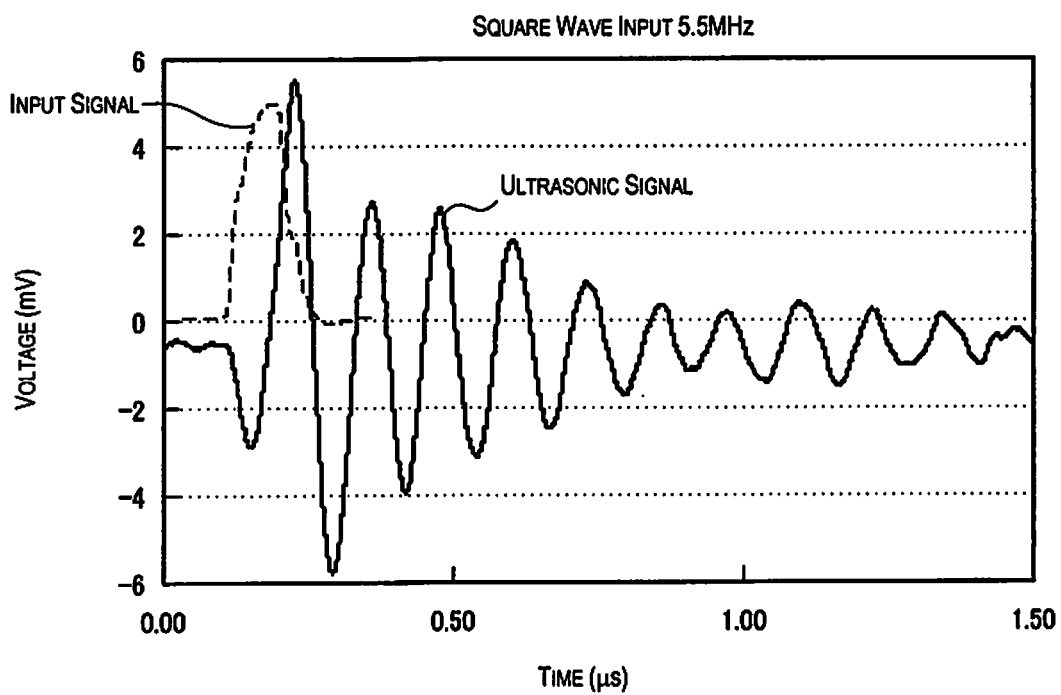

FIG. 4A and FIG. 4B show an ultrasonic signal waveform in a case that a square wave of frequencies 2.5 MHz and 5.5 MHz is inputted to an ultrasonic element of resonance frequency 5.5 MHz. The broken line indicates a square wave signal and the continuous line indicates an ultrasonic wave signal.

In FIG. 4A, a time (pulse width) from the rise of the input signal to the fall of the input signal corresponds to approximately 2 cycles of the vibration of the vibrating membrane. Thus, even though it is the square wave of 2.5 MHz, the ultrasonic element of resonance frequency 5.5 MHz can be driven. This is the reason that the maximum amplitudes of the ultrasonic waves in the frequency region lower than the resonance frequency become large as shown in FIG. 2A and FIG. 3A. On the other hand, in FIG. 4B, the pulse width of the input signal corresponds to 1 cycle of the vibration of the vibrating membrane so that the ultrasonic wave of resonance frequency 5.5 MHz is outputted.

Figure 5A:
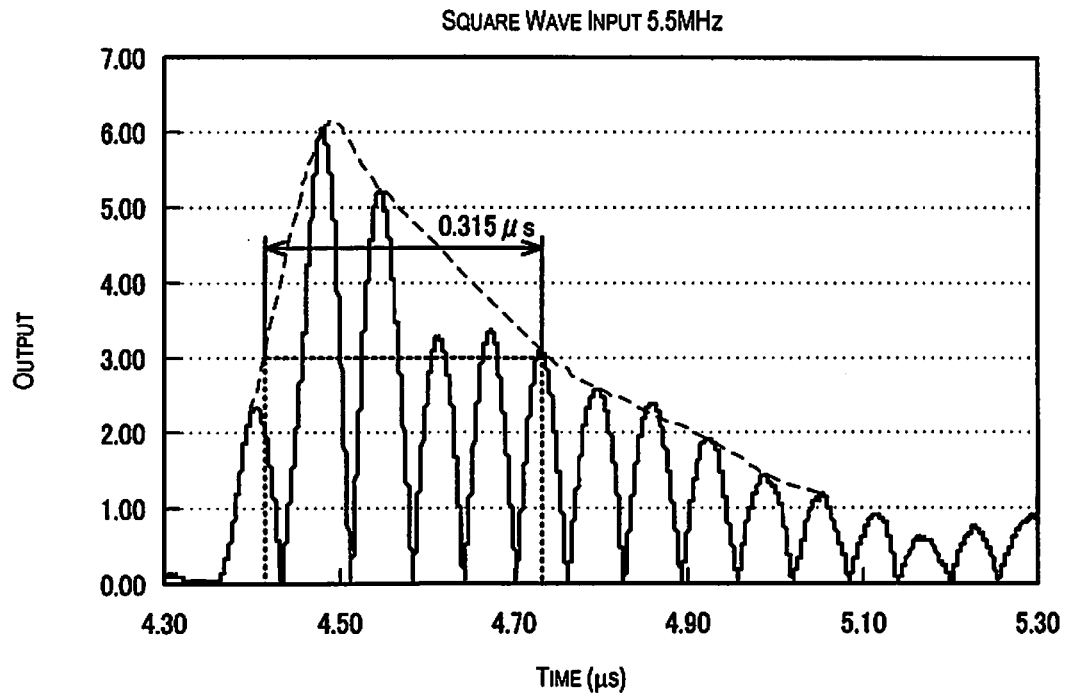
FIG. 5A and FIG. 5B show an absolute value of an ultrasonic signal and an envelope demodulation signal waveform in a case that a square wave and a sine wave of frequency 5.5 MHz are inputted to an ultrasonic element of resonance frequency 5.5 MHz.
Figure 5B:
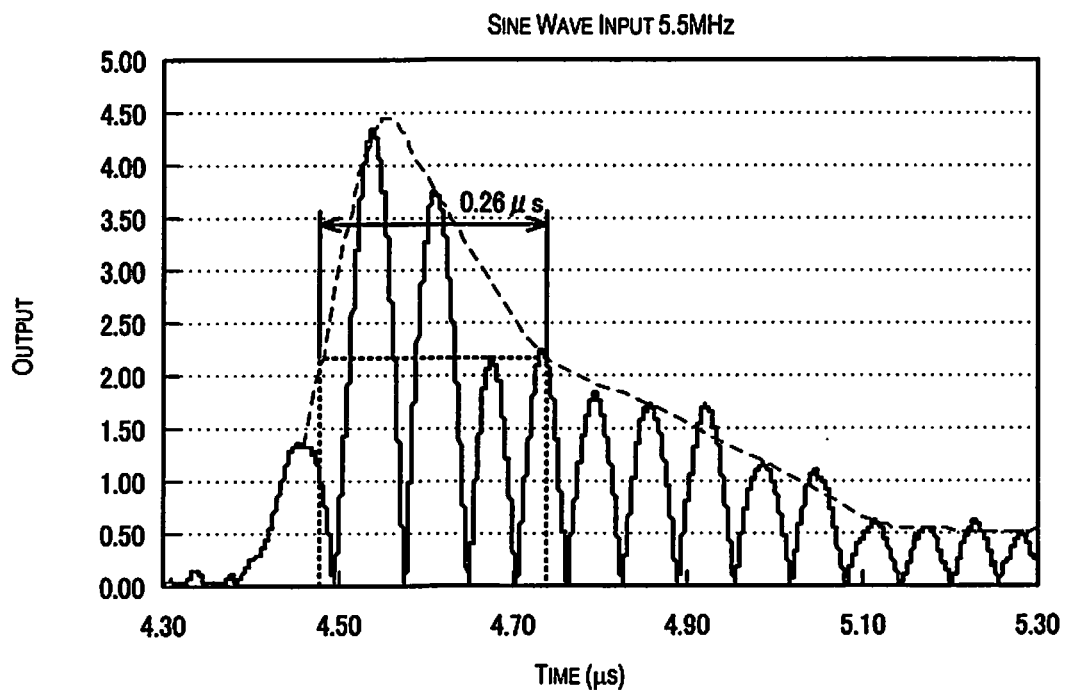

FIG. 5A and FIG. 5B show an absolute value of an ultrasonic signal and an envelope demodulation signal waveform in a case that a square wave and a sine wave of frequency 5.5 MHz are inputted to an ultrasonic element of resonance frequency 5.5 MHz. In each drawing, the continuous line indicates an absolute value of an ultrasonic signal and the broken line indicates an envelope demodulation signal. In addition, each drawing shows a time width (half bandwidth) as to become a half value (a value of ½) of a maximum value (peak value) of an envelope demodulation signal.

As shown in FIG. 5A and FIG. 5B, the half bandwidth is 0.315 μs in a case of the square wave input. On the other hand, the half bandwidth is 0.26 μs in a case of the sine wave input. The half bandwidth is shorter, and this means that the time from the rise of the intensity of the ultrasonic signal to the fall of the intensity of the ultrasonic signal is short.

Figure 6A:
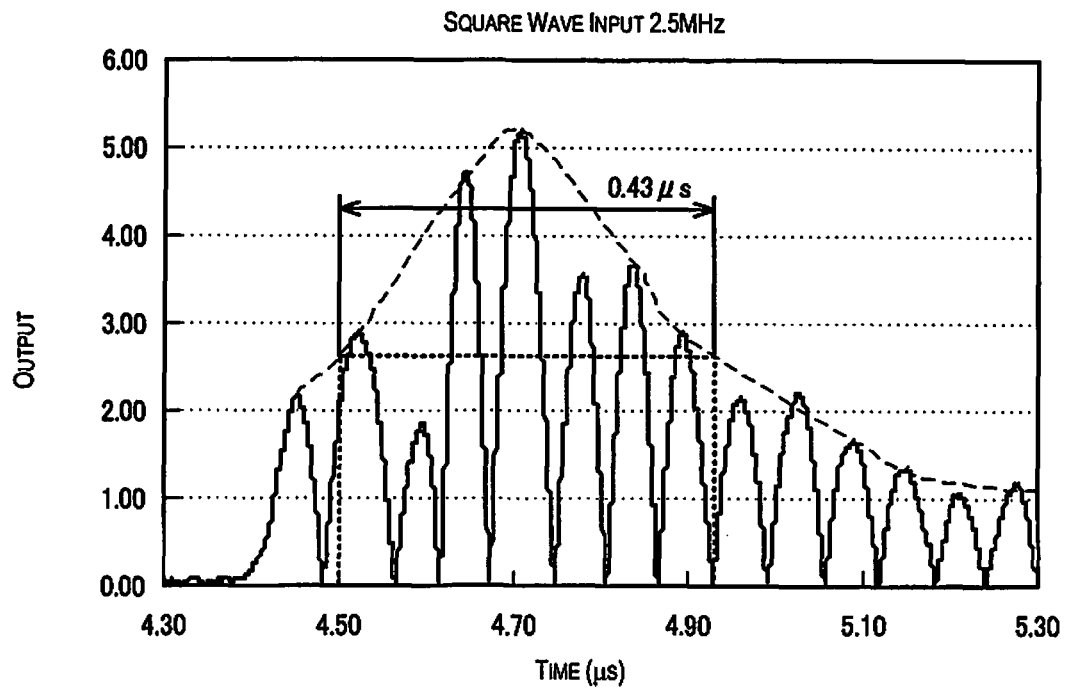
FIG. 6A and FIG. 6B show an absolute value of an ultrasonic signal and an envelope demodulation signal waveform in a case that a square wave and a sine wave of frequency 2.5 MHz are inputted to an ultrasonic element of resonance frequency 5.5 MHz.
Figure 6B:
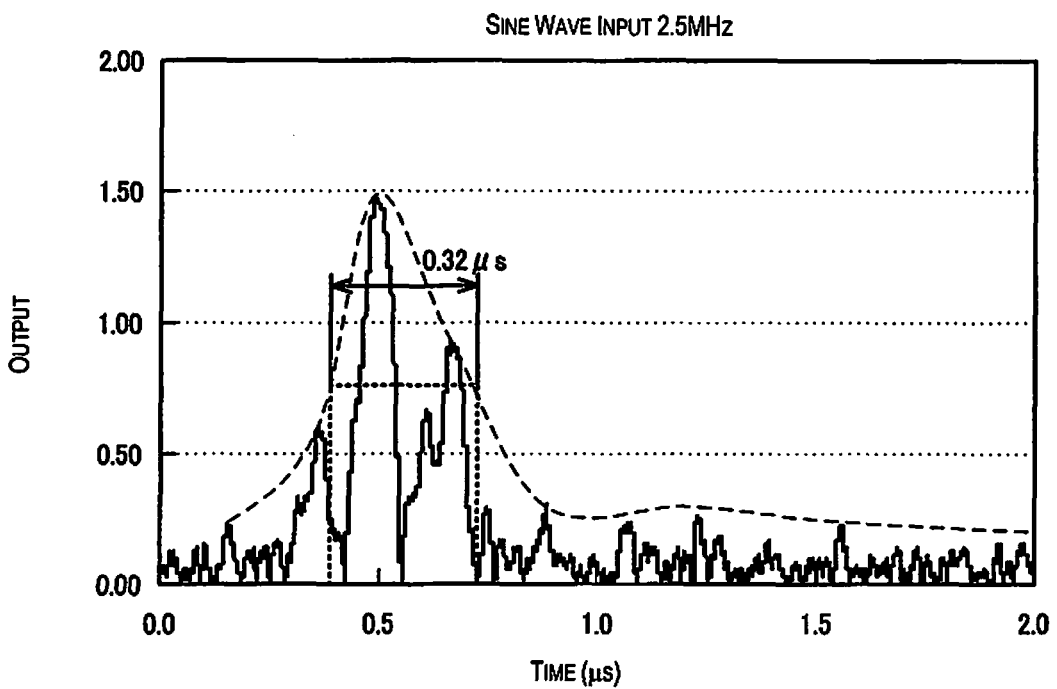

FIG. 6A and FIG. 6B show an absolute value of an ultrasonic signal and an envelope demodulation signal waveform in a case that a square wave and a sine wave of frequency 2.5 MHz are inputted to an ultrasonic element of resonance frequency 5.5 MHz.

As shown in FIG. 6A and FIG. 6B, an absolute value of an ultrasonic signal in a case of the square wave input is larger than an absolute value of an ultrasonic signal in a case of the sine wave input, and that is, the intensity of the ultrasonic wave is high. As described in FIG. 4A, it is because the time (pulse width) from the rise of the square wave signal to the fall of the square wave signal corresponds to 2 cycles of the vibration of the vibrating membrane. Also, in the same manner as FIG. 5A and FIG. 5B, the half bandwidth is 0.43 μs in a case of the square wave input. On the other hand, the half bandwidth is 0.32 μs in a case of the sine wave input so that it becomes smaller.

Because of this, in a case of the square wave input, the time from the rise of the intensity of the ultrasonic signal to the fall of the intensity of the ultrasonic signal becomes longer, and in a case of the sine wave input, the time from the rise of the intensity of the ultrasonic signal to the fall of the intensity of the ultrasonic signal becomes shorter. In a case that a distance between the ultrasonic element and an object is close, the intensity of the ultrasonic wave can be low because the attenuation of the intensity is small when an ultrasonic wave outputted from the ultrasonic element reaches to the object and the reflected wave is returned to the ultrasonic element. On the other hand, the time from the timing that the ultrasonic wave is transmitted to the timing that the reflected wave (echo) is received becomes shorter because the distance is close. When the time from the rise of the intensity of the transmitted ultrasonic wave signal to the fall of the intensity of the transmitted ultrasonic wave signal becomes longer, it is difficult to obtain the desired resolution because the received echo signal and the transmitted ultrasonic wave signal are overlapped. Accordingly, in a case that a distance between the ultrasonic element and an object is close, to obtain the desired resolution, it has an advantage that the ultrasonic element that the resonance frequency is high is driven by the sine wave.

As described above, to obtain the desired resolution, in a case that a distance between the ultrasonic element and an object is far, it has an advantage that the ultrasonic element that the resonance frequency is low is driven by the square wave, and on the other hand, in a case that a distance between the ultrasonic element and an object is close, it has an advantage that the ultrasonic element that the resonance frequency is high is driven by the sine wave.

2. Ultrasonic Device

Figure 7:
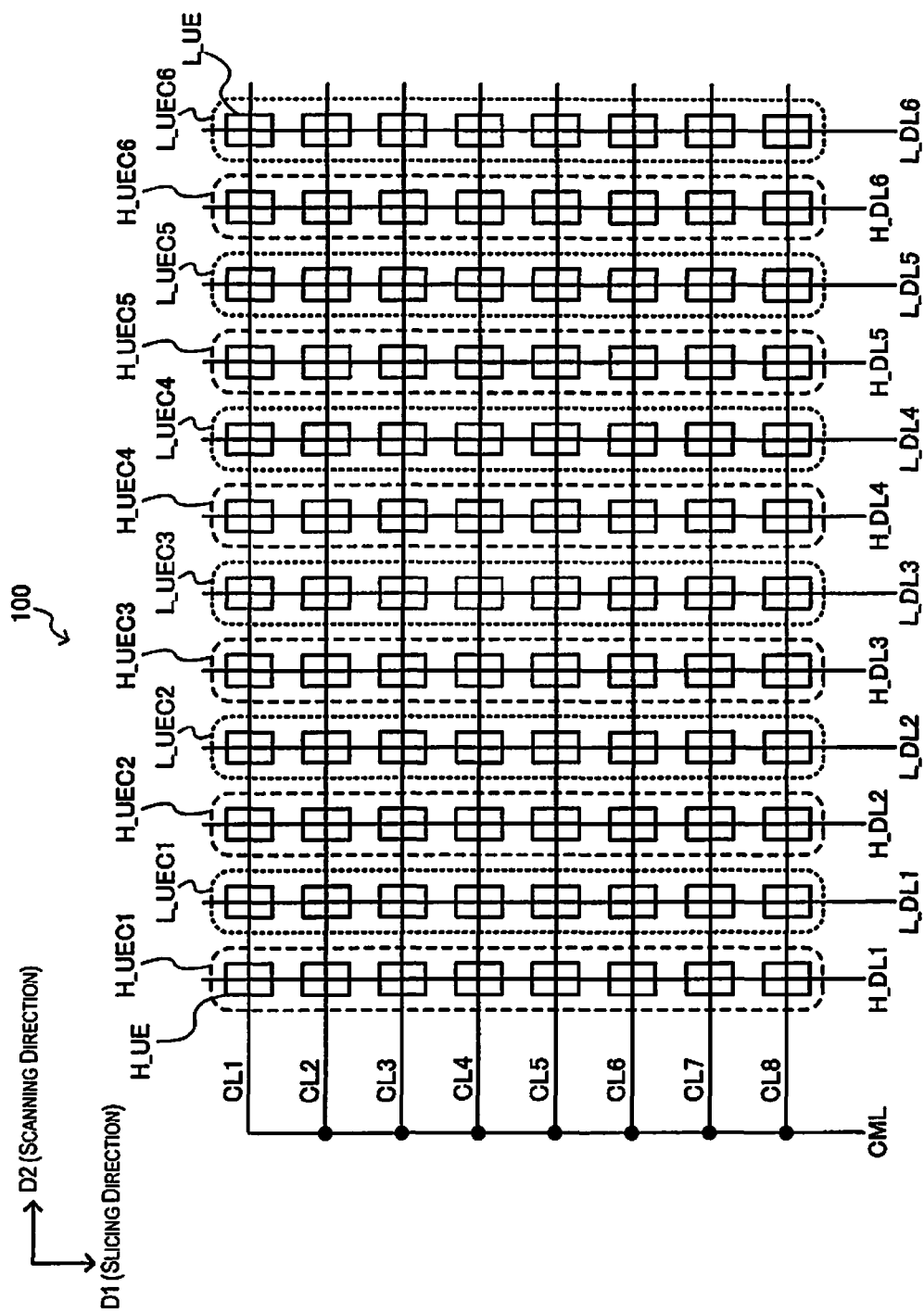
FIG. 7 shows a configuration example of an ultrasonic device.

FIG. 7 shows a configuration example of an ultrasonic device. The ultrasonic device of the present configuration example includes the first to n-th (n is integer number of more than 2) high-frequency ultrasonic element lines H_UEC1 to H_UECn, the first to n-th (n is integer number of more than 2) low-frequency ultrasonic element lines L_UEC1 to L_UECn, the first to n-th high-frequency drive electrode wires H_DL1 to H_DLn, the first to n-th low-frequency drive electrode wires L_DL1 to L_DLn, and the first to m-th (m is integer number of more than 2) common electrode wires CL1 to CLm (in the broad sense, a plurality of common electrode wires). In a case of FIG. 7, it indicates, for example, m=8, n=6, but it can be other values. By the way, the ultrasonic device 100 of the present embodiment is not limited to the configuration of FIG. 7, and various modifications such as omitting a part of the configuration elements, replacing to other configuration elements, adding other configuration elements, and the like are possible.

The first to n-th high-frequency ultrasonic element lines H_UEC1 to H_UECn include a plurality of ultrasonic elements H_UE having a resonance characteristic of the first frequency that are arranged along the first direction D1. The first to n-th high-frequency ultrasonic element lines H_UEC1 to H_UECn are arranged along the second direction, which intersects with the first direction D1. The ultrasonic elements H_UE having a resonance characteristic of the first frequency are the ultrasonic element as shown in FIG. 1A and FIG. 1B, and the length LOP of the short side of its opening OP is shorter than the length LOP of the short side of the opening OP of the ultrasonic elements L_UE having a resonance characteristic of the second frequency.

The first frequency is, for example, 5.5 MHz, and the second frequency is, for example, 1.5 MHz, but it can be other than those frequencies. Also, the length LOP of the short side of the opening OP of the ultrasonic elements H_UE having a resonance characteristic of the first frequency is, for example, 25 µm, and the length LOP of the short side of the opening OP of the ultrasonic elements L-UE having a resonance characteristic of the second frequency is, for example, 50 µm, but it can be other than those lengths.

The first to n-th low-frequency ultrasonic element lines L_UEC1 to L_UECn include a plurality of ultrasonic elements L_UE having a resonance characteristic of the second frequency, which is lower than the first frequency, that are arranged along the first direction D1. And, the first to n-th low-frequency ultrasonic element lines L_UEC1 to L_UECn are arranged along the second direction D2. The ultrasonic elements L_UE having a resonance characteristic of the second frequency are the ultrasonic element as shown in FIG. 1A and FIG. 1B, and the length LOP of the short side of its opening OP is longer than the length LOP of the short side of the opening OP of the ultrasonic elements H_UE having a resonance characteristic of the first frequency.

The first to n-th high-frequency ultrasonic element lines H_UEC1 to H_UECn and the first to n-th low-frequency ultrasonic element lines L_UEC1 to L_UECn are alternately arranged along the second direction D2. For example, as shown in FIG. 7, it is arranged in order of H_UEC1, L_UEC1, H_UEC2, L_UEC2, . . . , H_UEC6, L_UEC6. However, it is not necessary to alternate the high-frequency ultrasonic element line and the low-frequency ultrasonic element line.

The first to n-th high-frequency drive electrode wires H_DL1 to H_DLn are wired along the first direction D1. And, the i-th (i is the integer number of 1≤i≤n) high-frequency drive electrode wire H_DLi is connected to the first electrode that is provided in each of the plurality of ultrasonic elements H_UE that configure the i-th high-frequency ultrasonic element line H_UECi.

The first to n-th low-frequency drive electrode wires L_DL1 to L_DLn are wired along the first direction D1. And, the j-th (j is the integer number of 1≤j≤n) low-frequency drive electrode wire L_DLj is connected to the first electrode that is provided in each of the plurality of ultrasonic elements L_UE that configure the i-th low-frequency ultrasonic element line L_UECj.

During a transmission period to output an ultrasonic wave, the first to n-th drive signals VDR1 to VDRn outputted from a processing device 200, which will be described later, are supplied to each ultrasonic element through the high-frequency drive electrode wires H_DL1 to H_DLn and the low-frequency drive electrode wires L_DL1 to L_DLn. Also, during a receiving period to receive an ultrasonic echo signal, a receiving signal from each ultrasonic element is outputted through the high-frequency drive electrode wires H_DL1 to H_DLn and the low-frequency drive electrode wires L_DL1 to L_DLn.

The first to m-th common electrode wires CL1 to CLm (in a broad sense, a plurality of common electrode wires) are wired along the second direction D2. The second electrode provided in each of the plurality of ultrasonic elements HUE that configure the i-th high-frequency ultrasonic element line H_UECi is connected to any one of the first to m-th common electrode wires CL1 to CLm. Also, the second electrode provided in each of the plurality of ultrasonic elements L_UE that configure the j-th low-frequency ultrasonic element line L_UECj is connected to any one of the first to m-th common electrode wires CL1 to CLm.

The first to m-th common electrode wires CL1 to CLm are commonly connected to a common voltage line CML, and the common voltage VCOM is supplied to the common voltage line CML. The common voltage VCOM can be a certain amount of DC voltage, and it does not have to be 0V, that is, ground electric potential (ground potential).

3. Processing Device

Figure 8:
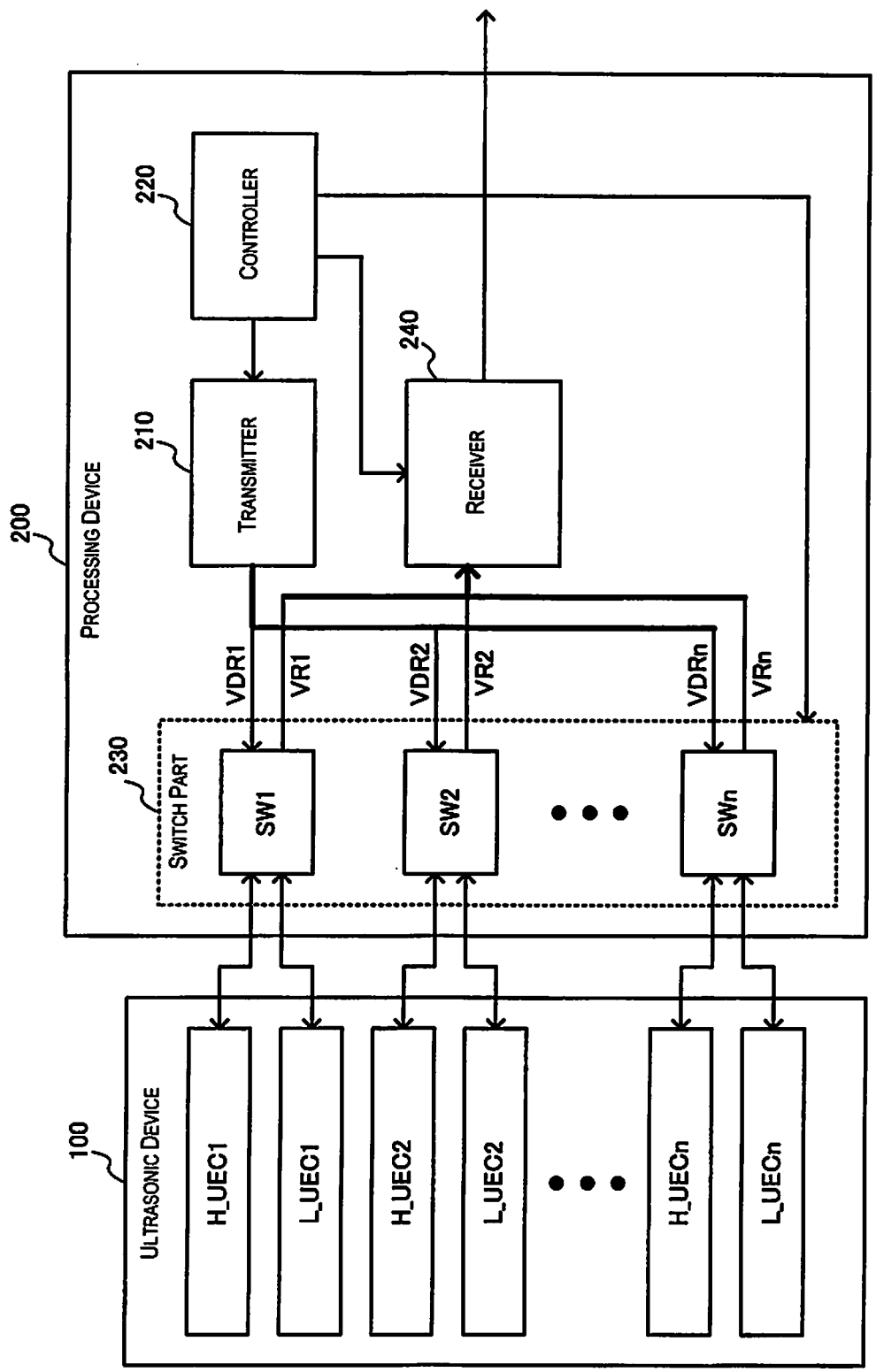
FIG. 8 shows a configuration example of a processing device.

FIG. 8 shows a configuration example of a processing device 200 of the present embodiment. The processing device 200 of the present embodiment is a processing device to perform processes of transmitting and receiving an ultrasonic wave to the ultrasonic device 100. This includes a transmitter 210, a controller 220, a switch part 230, and a receiver 240. By the way, the processing device 200 of the present embodiment is not limited to the configuration of FIG. 8, and various modifications such as omitting a part of the configuration elements, replacing to other configuration elements, adding other configuration elements, and the like are possible.

The transmitter 210 outputs the first to n-th driving signals VDR1 to VDRn (in the broad sense, driving signals) to the first to n-th high-frequency drive electrode wires H_DL1 to H_DLn of the ultrasonic device 100 and the first to n-th low-frequency drive electrode wires L_DL1 to L_DLn (in the broad sense, drive electrode wires) of the ultrasonic device 100 through the switch 230.

Concretely, the transmitter 210 outputs sine wave driving signals VDR1 to VDRn to the high-frequency ultrasonic element lines H_UEC1 to H_UECn in the first mode. In the second mode, the transmitter 210 outputs square wave driving signals VDR1 to VDRn to the low-frequency ultrasonic element lines L_UEC1 to L_UECn. Also, in the third mode, the transmitter 210 outputs the square wave driving signals VDR1 to VDRn to both of the high-frequency ultrasonic element lines H_UEC1 to H_UECn and the low-frequency ultrasonic element lines L_UEC1 to L_UECn. The transmitter 210 can be configured by, for example, a pulse generator, an amplification equipment, and the like.

In the first mode, the sine wave driving signals VDR1 to VDRn can be outputted to the high-frequency ultrasonic element lines H_UEC1 to H_UECn so that as described above, in a case that a distance between the ultrasonic element and an object is close, the high resolution can be obtained. In the second mode, the square wave driving signals VDR1 to VDRn can be outputted to the low-frequency ultrasonic element lines L_UEC1 to L_UECn so that in a case that a distance between the ultrasonic element and an object is far, the high resolution can be obtained. Also, in the third mode, the square wave driving signals VDR1 to VDRn can be outputted to both of the high-frequency ultrasonic element lines H_UEC1 to H_UECn and the low-frequency ultrasonic element lines L_UEC1 to L_UECn so that this can be used in a case that a distance between the ultrasonic element and an object is unclear, or in a case that it desires to detect both a close object and a far object.

Figure 10:
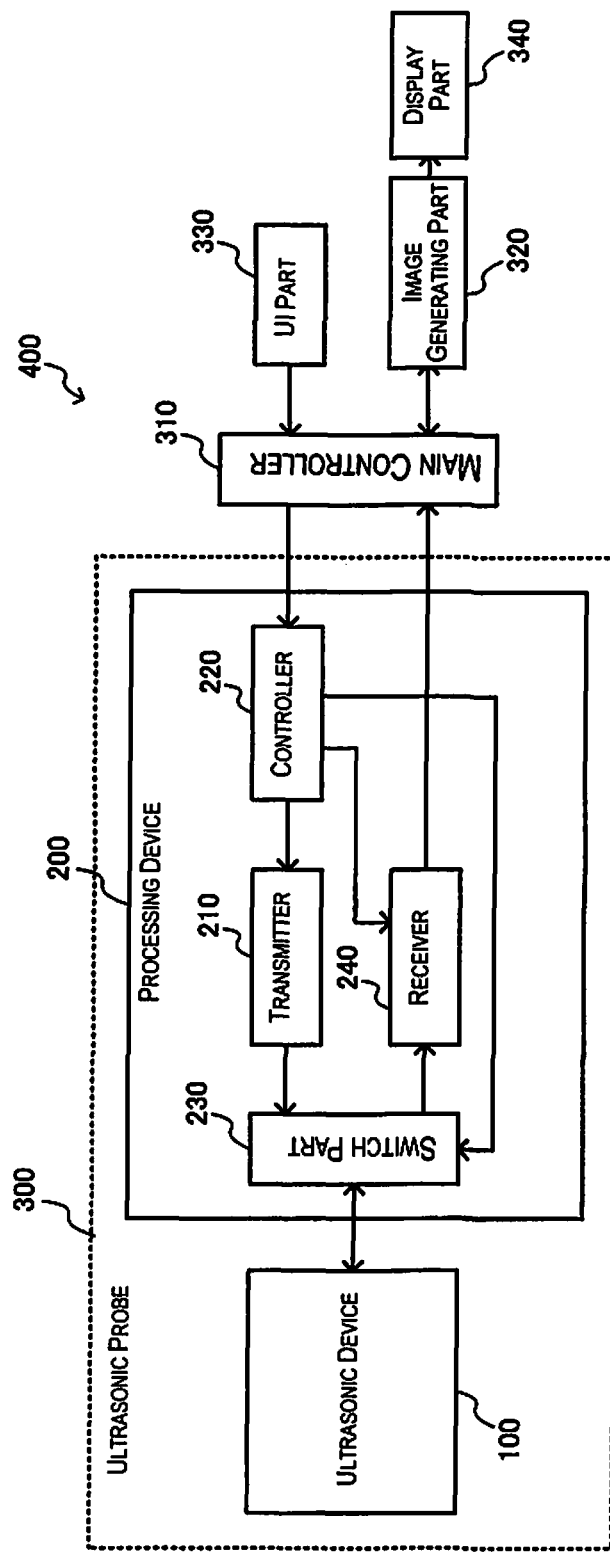
FIG. 10 shows a basic configuration example of an ultrasonic probe and an ultrasonic diagnostic device.

The receiver 240 performs a receiving process of the receiving signals VR1 to VRn from the ultrasonic device 100 through the switch part 230. Concretely, it performs amplifying the receiving signals, gain setting, frequency setting, A/D conversion (Analog/Digital conversion), and the like, and it is outputted to an image generating part 320 as detected data (detected information) (FIG. 10). The receiver 240 can be configured by a low noise amplifier, a voltage-controlled attenuator, a programmable gain amplifier, a low-pass filter, an A/D converter, and the like.

The controller 220 controls the transmitter 210, the receiver 240, and the switch 230. Concretely, the controller 220 controls the generating and outputting processes of the driving signals VDR1 to VDRn to the transmitter 210, and the receiving process of the receiving signals VR1 to VRn to the receiver 240, and the controller 220 controls the switch part 230 to switch transmitter and receiver and to switch the high-frequency ultrasonic element line H_UECi and the low-frequency ultrasonic element line L_UECi. The controller 220 can be realized by, for example, FPGA (Field-Programmable Gate Array).

The switch part 230 selects at least one of the high-frequency ultrasonic element lines H_UEC1 to H_UECn and the low-frequency ultrasonic element lines L_UEC1 to L_UECn based on the control of the controller 220, and the driving signals VDR1 to VDRn are outputted to a selected ultrasonic element line from the transmitter 210.

Concretely, the switch part 230 selects the high-frequency ultrasonic element lines H_UEC1 to H_UECn in the first mode. And, during the transmitting period in the first mode, the driving signals VDR1 to VDRn are outputted to the high-frequency ultrasonic element lines H_UEC1 to H_UECn from the transmitter 210. Also, during the receiving period in the first mode, the receiving signals VR1 to VRn are received from the high-frequency ultrasonic element lines H_UEC1 to H_UECn, and it is outputted to the receiver 240.

The switch part 230 selects the low-frequency ultrasonic element lines L_UEC1 to L_UECn in the second mode. And, during the transmitting period in the second mode, the driving signals VDR1 to VDRn are outputted to the low-frequency ultrasonic element lines L_UEC1 to L_UECn from the transmitter 210. Also, during the receiving period in the second mode, the receiving signals VR1 to VRn are received from the low-frequency ultrasonic element lines L_UEC1 to L_UECn, and it is outputted to the receiver 240.

The switch part 230 selects both of the high-frequency ultrasonic element lines H_UEC1 to H_UECn and the low-frequency ultrasonic element lines L_UEC1 to L_UECn in the third mode. And, during the transmitting period in the third mode, the driving signals VDR1 to VDRn are outputted to both of the high-frequency ultrasonic element lines H_UEC1 to H_UECn and the low-frequency ultrasonic element lines L_UEC1 to L_UECn from the transmitter 210. Also, during the receiving period in the third mode, the receiving signals VR1 to VRn are received from both of the high-frequency ultrasonic element lines H_UEC1 to H_UECn and the low-frequency ultrasonic element lines L_UEC1 to L_UECn, and it is outputted to the receiver 240.

More specifically, the switch part 230 includes switch circuits SW1 to SWn. For example, in the first mode, the SW1 selects the first high-frequency ultrasonic element line H_UEC1. In the second mode, it selects the first low-frequency ultrasonic element line L_UEC1. In the third mode, it selects both of the first high-frequency ultrasonic element line H_UEC1 and the first low-frequency ultrasonic element line L_UEC1.

Figure 9A:
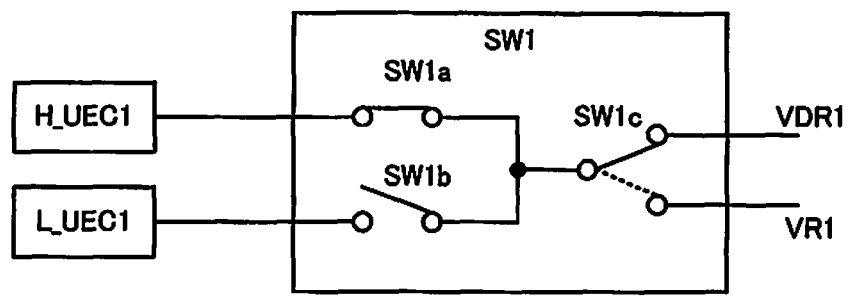
FIG. 9A, FIG. 9B, and FIG. 9C show configuration examples of switch circuits.
Figure 9B:
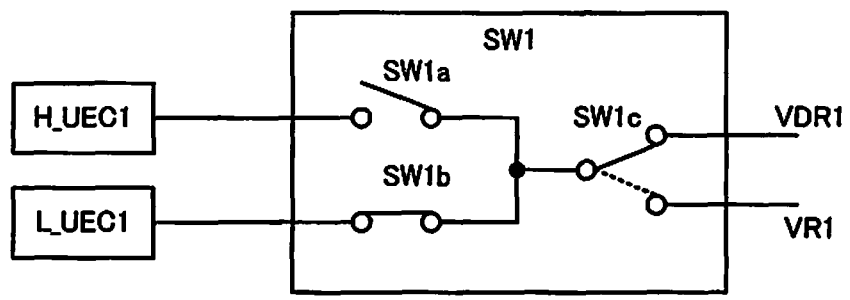
Figure 9C:
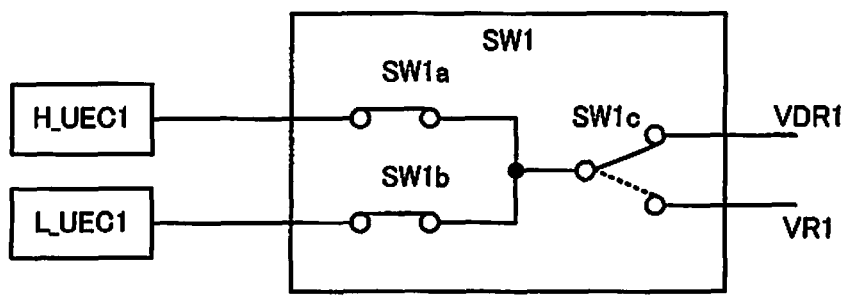

FIG. 9A, FIG. 9B, and FIG. 9C show configuration examples of switch circuits. The switch circuit SW1 includes switch elements SW1a, SW1b, SW1c. By the way, the switch circuit SW1 of the present embodiment is not limited to the configuration of FIGS. 9A-9C, and various modifications such as omitting a part of the configuration elements, replacing to other configuration elements, adding other configuration elements, and the like are possible.

FIG. 9A shows a case of the first mode. In the first mode, the SW1a is set in on-state and the SW1b is set in off-state so that the high-frequency ultrasonic element line H_UEC1 is selected. And, during the transmitting period, the SW1c is set in a state as indicated by the continuous line, and the driving signal VDR1 is outputted to the high-frequency ultrasonic element line H_UEC1 from the transmitter 210. Also, during the receiving period, the SW1c is set in a state as indicated by the broken line, and the receiving signal VR1 is outputted to the receiver 240 from the high-frequency ultrasonic element line H_UEC1.

FIG. 9B shows a case of the second mode. In the second mode, the SW1a is set in off-state and the SW1b is set in on-state so that the low-frequency ultrasonic element line L_UEC1 is selected. And, during the transmitting period, the SW1c is set in a state as indicated by the continuous line, and the driving signal VDR1 is outputted to the low-frequency ultrasonic element line L_UEC1 from the transmitter 210. Also, during the receiving period, the SW1c is set in a state as indicated by the broken line, and the receiving signal VR1 is outputted to the receiver 240 from the low frequency ultrasonic element line L_UEC1.

FIG. 9C shows a case of the third mode. In the third mode, both of the SW1a and the SWb1 are set in on-state so that both of the high-frequency ultrasonic element line H_UEC1 and the low-frequency ultrasonic element line L_UEC1 are selected. And, during the transmitting period, the SW1c is set in a state as indicated by the continuous line, and the driving signal VDR1 is outputted to both of the high-frequency ultrasonic element line H_UEC1 and the low-frequency ultrasonic element line L_UEC1 from the transmitter 210. Also, during the receiving period, the SW1c is set in a state as indicated by the broken line, and the receiving signal VR1 is outputted to the receiver 240 from both of the high-frequency ultrasonic element line H_UEC1 and the low-frequency ultrasonic element line L_UEC1.

By the way, regarding other switch circuits SW2 to SWn, it can be the same configurations as FIG. 9A, FIG. 9B, and FIG. 9C.

As described above, according to the ultrasonic device 100 and the processing device 200 of the present embodiment, in the first mode, a sine wave driving signal can be outputted to the high-frequency ultrasonic element lines. In the second mode, a square wave driving signal can be outputted to the low-frequency ultrasonic element lines. In this way, the first mode is used for an object which is close to the ultrasonic device 100, and the second mode is used for an object which is far from the ultrasonic device 100 so that the desired resolution can be obtained for either case. Also, in the third mode, a square wave driving signal can be outputted to both of the high-frequency ultrasonic element lines and the low-frequency ultrasonic element lines. In this way, the desired resolution can be obtained in a case that a distance between the ultrasonic element and an object is unclear, or in a case that it desires to detect both of an object in close distance and an object in far distance, or the like.

4. Ultrasonic Probe and Ultrasonic Diagnostic Device

FIG. 10 shows a basic configuration example of an ultrasonic probe 300 and an ultrasonic diagnostic device 400. The ultrasonic probe 300 includes the ultrasonic device 100 and the processing device 200. The ultrasonic diagnostic device 400 includes the ultrasonic probe 300, a main controller 310, an image generating part 320, a User Interface (UI) part 330, and a display part 340. By the way, it can be a configuration that the ultrasonic device 100 can be released or can be replaced from the ultrasonic probe 300.

The main controller 310 controls the ultrasonic probe 300 to perform the ultrasonic wave transmitting and receiving control, and it controls the image generating part 320 to perform an image processing of the detected data, and the like. By the way, a part of the control performed by the main controller 310 can be performed by the controller 220 of the processing device 200, and a part of the control performed by the controller 220 can be performed by the main controller 310 of the ultrasonic diagnostic device 400.

The image generating part 320 receives detection data from the receiving part 240, performs the necessary image processing, and generates image data for a display. Specifically, the image generating part 320 generates the first image data based on a receiving signal from the high-frequency ultrasonic element lines H_UEC1 to H_UECn in the first mode, and the image generating part 320 generates the second image data based on a receiving signal from the low-frequency ultrasonic element lines L_UEC1 to L_UECn in the second mode. Also, in the third mode, the third image data is generated based on a receiving signal from the high-frequency ultrasonic element lines H_UEC1 to H_UECn and the low-frequency ultrasonic element lines L_UEC1 to L_UECn. In addition, it performs an image processing to synthesize the first image data and the second image data.

The first image data contains an image that a desired resolution can be obtained for an object located in a range of the first distance. The second image data contains an image that a desired resolution can be obtained for an object located in a range of the second distance that is farther than the range of the first distance. Also, the third image data contains an image that a desired resolution can be obtained for an object located in the ranges of both of the first and second distances, and for an object located in a middle of the ranges of the first and second distances. For example, the range of the first distance is 1 to 5 cm, and the range of the second distance is 10 to 15 cm.

In this way, by generating the first image data in the first mode for an object in a close distance, and by generating the second image data in the second mode for an object in a far distance, the desired resolution can be obtained for either case. Also, in a case that a distance to an object is unclear, or in a case that a detection for an object in a wide range of distance between a close distance to a far distance is desired, by generating the third image data in the third mode, the desired resolution can be obtained. In addition, by performing an image processing to synthesize the first image data and the second image data, an object in a close distance and an object in a far distance can be efficiently displayed in one screen.

The User Interface (UI) part 330 outputs a necessary command (command) to the main control part 310 based on the user's control (e.g., touch panel control, or the like). The display part 340 is, for example, a liquid crystal display, and the like, and it displays image data for display generated from the image generating part 320.

Figure 11:
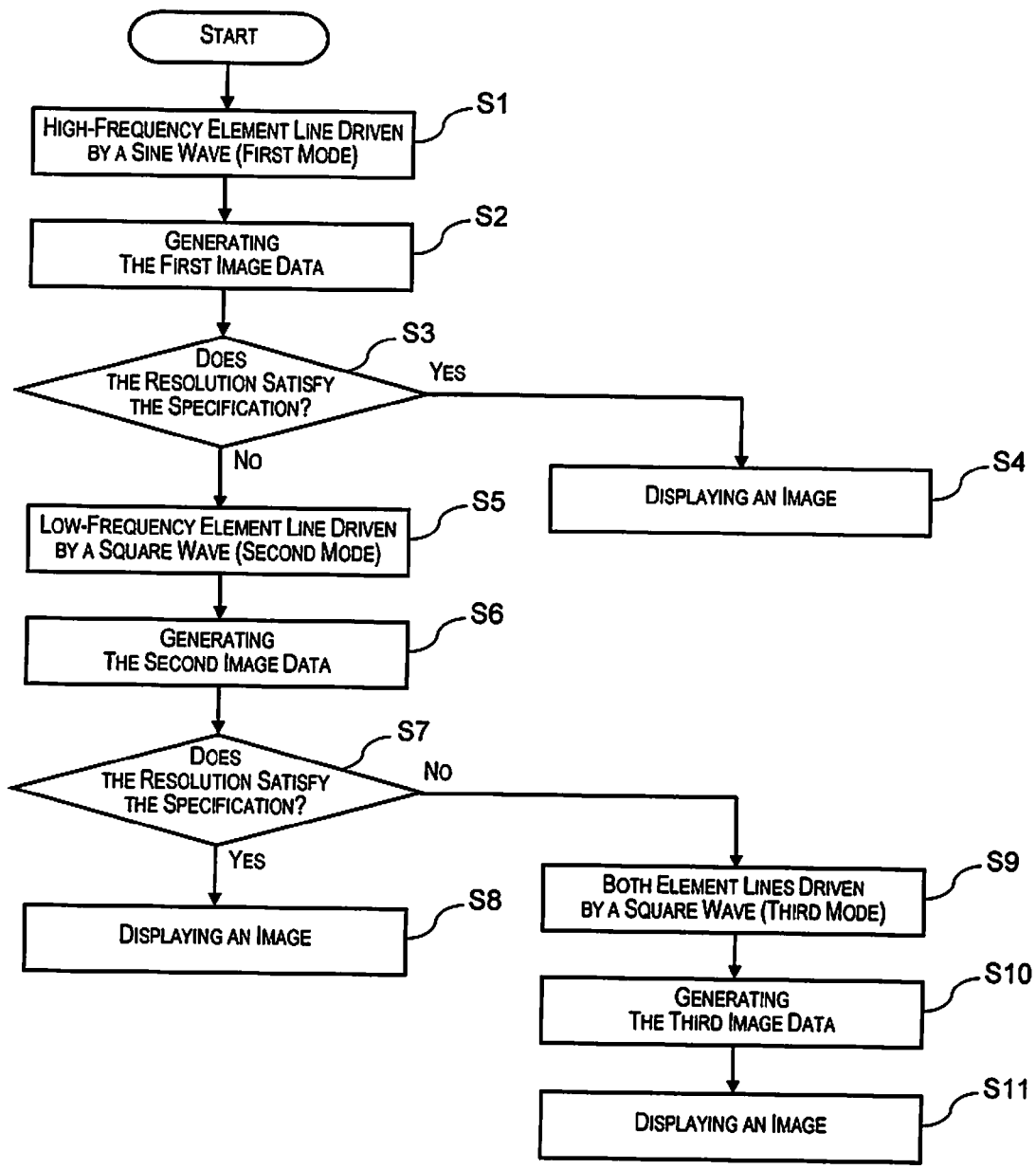
FIG. 11 is the first flowchart showing a flow of driving and image generation in an ultrasonic diagnostic device.

FIG. 11 is the first flowchart showing a flow of driving and image generation in an ultrasonic diagnostic device 400 of the present embodiment. The flow shown in FIG. 11 is executed by the controller 220 and the main controller 310.

First, the first mode is executed (Step S1). That is, the switch part 230 selects the high-frequency ultrasonic element lines, and the transmitter 210 drives the high-frequency ultrasonic element lines by a sine wave through the switch part 230. And, the receiver 240 receives a receiving signal from the high-frequency ultrasonic element lines through the switch part 230 so as to perform the receiving process.

Next, the image generating part 320 receives detection data from the receiving part 240 and generates the first image data (Step S2). The main control part 310 determines whether or not the resolution satisfies the specification for the first image data (Step S3). The evaluation of the resolution can be performed by, for example, a contrast detection used for an autofocus in a digital camera, or the like. That is, the contrast is detected from the image data, and when the detected contrast is more than the predetermined value, it determines that the resolution satisfies the specification. When the detected contrast is less than the predetermined value, it determines that the resolution does not satisfy the specification. When the resolution satisfies the specification, the display part 340 displays the first image data (Step S4).

On the other hand, in a case that the resolution does not satisfy the specification, the second mode is executed (Step S5). That is, the switch part 230 selects the low-frequency ultrasonic element lines, and the transmitter 210 drives the low-frequency ultrasonic element lines by a square wave through the switch part 230. And, the receiver 240 receives a receiving signal from the low-frequency ultrasonic element lines through the switch part 230 so as to perform the receiving process.

Next, the image generating part 320 receives the detection data from the receiving part 240 and generates the second image data (Step S6). The main controller 310 determines whether or not the resolution satisfies the specification for the second image data (Step S7). When the resolution satisfies the specification, the display part 340 displays the second image data (Step S8).

On the other hand, when the resolution does not satisfy the specification, the third mode is executed (Step S9). That is, the switch part 230 selects both of the high-frequency ultrasonic element lines and the low-frequency ultrasonic element lines, and the transmitter 210 drives both of the high-frequency ultrasonic element lines and the low-frequency ultrasonic element lines by a square wave through the switch part 230. And, the receiver 240 receives a receiving signal from both of the high-frequency ultrasonic element lines and the low-frequency ultrasonic element lines through the switch part 230 so as to perform the receiving process.

Next, the image generating part 320 receives the detection data from the receiving part 240 and generates the third image data (Step S10), and the display part 340 displays the third image data (Step S11).

As described, according to the ultrasonic diagnostic device 400 of the present embodiment, the first, the second, and the third modes are automatically switched in response to a distance to an object to be detected and it can perform probing. In this way, regardless a distance to an object to be detected, a clear echo image can be obtained so that an accurate diagnosis becomes possible.

Figure 12:
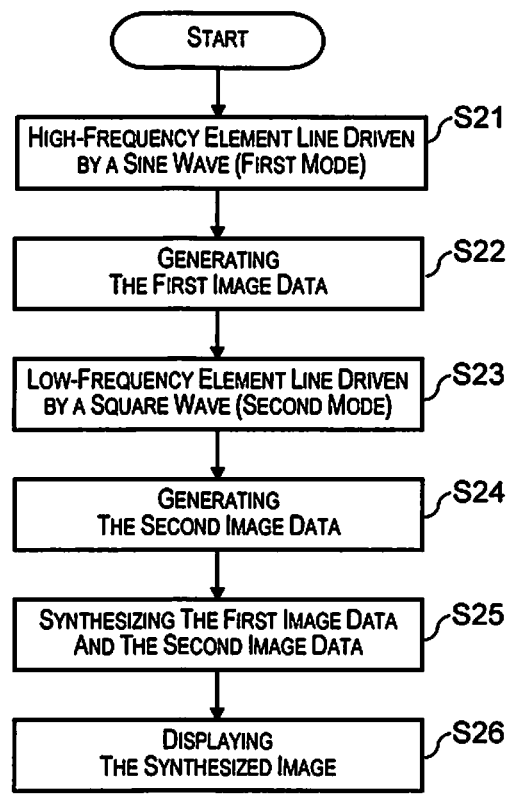
FIG. 12 is the second flowchart showing a flow of driving and image generation in an ultrasonic diagnostic device.

FIG. 12 is the second flowchart showing a flow of driving and image generation in an ultrasonic diagnostic device 400 of the present embodiment. The flow shown in FIG. 12 is executed by the controller 220 and the main controller 310 in the same manner as the flow of FIG. 11.

First, the first mode is executed (Step S21). That is, the switch part 230 selects the high-frequency ultrasonic element lines, and the transmitter 210 drives the high-frequency ultrasonic element lines by a sine wave through the switch part 230. And, the receiver 240 receives a receiving signal from the high-frequency ultrasonic element lines through the switch part 230 so as to perform the receiving process.

And, the image generating part 320 receives the detection data from the receiver 240 and generates the first image data (Step S22).

Next, the second mode is executed (Step S23). That is, the switch part 230 selects the low-frequency ultrasonic element lines, and the transmitter 210 drives the low-frequency ultrasonic element lines by a square wave through the switch part 230. And, the receiver 240 receives a receiving signal from the low-frequency ultrasonic element lines through the switch part 230 so as to perform the receiving process.

And, the image generating part 320 receives the detection data from the receiver 240 and generates the second image data (Step S24).

Next, the image generating part 320 synthesizes the first image data and the second image data (Step S25), and the display part 340 displays the synthesized image data (Step S26).

As described, according to the ultrasonic diagnostic device 400 of the present embodiment, by synthesizing an image in the first mode and an image in the second mode, an object in a close distance and an object in a far distance can be efficiently displayed in one screen.

Figure 13A:
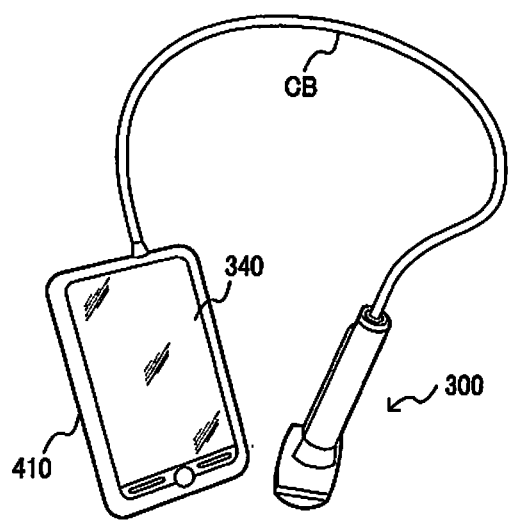
FIG. 13A and FIG. 13B are concrete configuration examples of ultrasonic diagnostic devices.
Figure 13B:
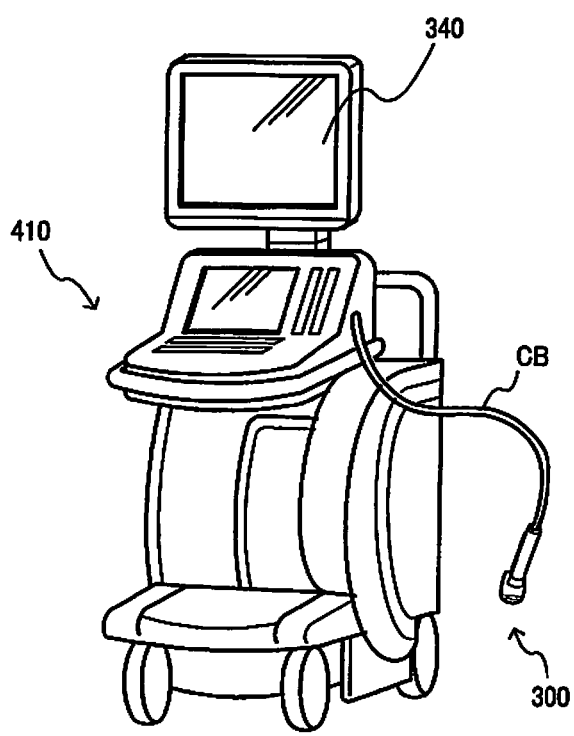

FIG. 13A and FIG. 13B show the concrete configuration examples of the ultrasonic diagnostic devices 400 of the present embodiment. FIG. 13A shows a portable type ultrasonic diagnostic device 400, and FIG. 13B shows a floor-standing type ultrasonic diagnostic device 400.

Both the portable type and the floor-standing type ultrasonic diagnostic devices 400 include the ultrasonic probe 300, a cable CB, and an ultrasonic diagnostic device main body 410. The ultrasonic probe 300 is connected to the ultrasonic diagnostic device main body 410 by the cable CB. The ultrasonic diagnostic device main body 410 includes the display part 340 that displays an image data for display.

Figure 13C:
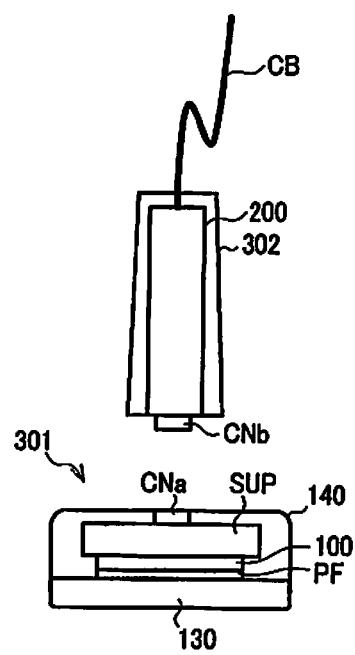
FIG. 13C is a concrete configuration example of an ultrasonic probe.

FIG. 13C is a concrete configuration example of the ultrasonic probe 300 of the present embodiment. The ultrasonic probe 300 includes the probe head 301 and the probe main body 302. As shown in FIG. 13C, the probe head 301 is releasable from the probe main body 302.

The probe head 301 includes the ultrasonic device 100, a supporting member SUP, a connecting member 130 that connects with a device under test, a protective member (protective film) that protects the ultrasonic device 100, and a connector CNa, and a probe case 140. The ultrasonic device 100 is provided between the connecting member 130 and the supporting member SUP.

The probe main body 302 includes the processing device 200 and the probe main body side connector CNb. The probe main body side connector CNb connects with the probe head side connector CNa. The probe main body 302 is connected to the ultrasonic diagnostic device main body by the cable CB.

While the present embodiment has been explained in detail as above, it will be apparent to those skilled in the art that various changes and modifications can be made herein without substantially departing from the subject matter and the effect of the invention. Therefore, such changes and modifications are included in the scope of the invention. For example, the terms used in the specification or the drawings at least once together with a different term having a broader or similar meaning can be replaced with the different term in any portion of the specification or the drawings. Also, the configurations and the operations of the processing device, the ultrasonic device, the ultrasonic probe, and the ultrasonic diagnostic device are not limited to the described present embodiment, and various changes and modifications are possible.

GENERAL INTERPRETATION OF TERMS

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:
1. An ultrasonic device comprising:
a substrate;
a plurality of first ultrasonic elements having a resonance characteristic of a first frequency disposed on the substrate; and
a plurality of second ultrasonic elements having a resonance characteristic of a second frequency, which is lower than the first frequency, disposed on the substrate,
the plurality of first ultrasonic elements being arranged along a first direction to make a first high-frequency ultrasonic element line to an n-th high-frequency ultrasonic element line (n is an integer of more than 2),
the plurality of second ultrasonic elements being arranged along the first direction to make a first low-frequency ultrasonic element line to an n-th low-frequency ultrasonic element line,
the first high-frequency ultrasonic element line to the n-th high-frequency ultrasonic element line being arranged along a second direction which intersects with the first direction,
the first low-frequency ultrasonic element line to the n-th low-frequency ultrasonic element line being arranged along the second direction,
each of the first ultrasonic elements and each of the second ultrasonic elements having an opening provided in the substrate, a vibrating membrane that covers the opening, and a piezo element part provided on the vibrating membrane, and
a length in the second direction of the opening of each of the first ultrasonic elements being shorter than a length in the second direction of the opening of each of the second ultrasonic elements.

2. The ultrasonic device according to claim 1, further comprising:
a first high-frequency drive electrode wire to an n-th high-frequency drive electrode wire arranged along the first direction;
a first low-frequency drive electrode wire to an n-th low-frequency drive electrode wire arranged along the first direction; and
a plurality of common electrode wires arranged along the second direction,
a first electrode, which is placed in each of the plurality of first ultrasonic elements configuring an i-th high-frequency ultrasonic element line (i is an integer of 1 or larger and n or smaller) among the first high-frequency ultrasonic element line to the n-th high-frequency ultrasonic element line, being connected to an i-th high-frequency drive electrode wire among the first high-frequency drive electrode wire to the n-th high-frequency drive electrode wire,
a second electrode, which is placed in each of the plurality of first ultrasonic elements configuring the i-th high-frequency ultrasonic element line, being connected to any one of the plurality of common electrode wires,
a third electrode, which is placed in each of the plurality of second ultrasonic elements configuring a j-th low-frequency ultrasonic element line (j is an integer of 1 or large and n or smaller) among the first low-frequency ultrasonic element line to the n-th low-frequency ultrasonic element line, being connected to a j-th low-frequency drive electrode wire among the first low-frequency drive electrode wire to the n-th low-frequency drive electrode wire, and
a fourth electrode, which is placed in each of the plurality of second ultrasonic elements configuring the j-th low-frequency ultrasonic element line, being connected to any of the plurality of common electric wires.

3. The ultrasonic device according to claim 2, wherein
the piezo element part has a lower electrode that is provided on the vibrating membrane,
a piezoelectric body film is provided to cover at least a part of the lower electrode,
an upper electrode is provided to cover at least a part of the piezoelectric body film,
the first electrode is one of the upper electrode and the lower electrode, and
the second electrode is the other of the upper electrode and the lower electrode.

4. The ultrasonic device according to claim 1, wherein
the first high-frequency ultrasonic element line to the n-th high-frequency ultrasonic element line and the first low-frequency ultrasonic element line to the n-th low-frequency ultrasonic element line are alternately arranged along the second direction.

5. An ultrasonic probe comprising the ultrasonic device according to claim 1.

6. An ultrasonic diagnostic device comprising:
the ultrasonic device according to claim 1;
the processing device configured to perform processing of ultrasonic wave transmission to the ultrasonic device; and
a display part configured to display image data for display.

* * * * *